United States Patent [19]
Dean et al.

[11] Patent Number: 6,022,857
[45] Date of Patent: *Feb. 8, 2000

[54] RADIOLABELED COMPOUNDS FOR THROMBUS IMAGING

[75] Inventors: Richard T. Dean; John Lister-James, both of Bedford, N.H.

[73] Assignee: Diatide, Inc., Londonderry, N.H.

[*] Notice: This patent is subject to a terminal disclaimer.

[21] Appl. No.: 09/100,537

[22] Filed: Jun. 19, 1998

Related U.S. Application Data

[63] Continuation-in-part of application No. 08/335,832, filed as application No. PCT/US93/04794, May 21, 1993, Pat. No. 5,925,331, and a division of application No. 08/253,317, Jun. 3, 1994, Pat. No. 5,830,856, which is a continuation-in-part of application No. 08/044,825, Apr. 8, 1993, abandoned, which is a continuation-in-part of application No. 07/653,012, Feb. 8, 1991, abandoned.

[51] Int. Cl.[7] .............................. A61K 38/00; C07K 5/00; C07K 7/00
[52] U.S. Cl. ............................ 514/12; 514/13; 514/14; 514/15; 514/16; 514/17; 514/18; 424/1.69; 424/1.11; 424/1.65
[58] Field of Search ................................ 424/1.69, 1.11, 424/1.65; 530/304, 300, 324, 325, 326, 327, 328, 329, 330; 534/10, 14; 514/12, 13, 14, 15, 16, 17, 18

[56] References Cited

U.S. PATENT DOCUMENTS

| 5,443,815 | 8/1995 | Dean et al. | 424/1.41 |
|---|---|---|---|
| 5,508,020 | 4/1996 | Dean et al. | 424/1.69 |
| 5,552,525 | 9/1996 | Dean | 530/326 |
| 5,645,815 | 7/1997 | Dean et al. | 424/1.69 |
| 5,736,122 | 4/1998 | Dean et al. | 424/1.69 |

*Primary Examiner*—Avis M. Davenport
*Attorney, Agent, or Firm*—Patricia A. McDaniels; Kevin E. Noonan

[57] ABSTRACT

This invention relates to radiolabeled scintigraphic imaging agents, and methods and reagents for producing such agents. Specifically, the invention relates to specific binding compounds, including peptides, that bind to a platelet receptor that is the platelet GPIIb/IIIa receptor, methods and kits for making such compounds, and methods for using such compounds labeled with technetium-99m via a covalently-linked radiolabel-binding moiety to image thrombi in a mammalian body.

11 Claims, 2 Drawing Sheets

SEQUENCE LISTING

<160> NUMBER OF SEQ ID NOS: 8

<210> SEQ ID NO 1
<211> LENGTH: 6
<212> TYPE: PRT
<213> ORGANISM: Artificial Sequence
<220> FEATURE:

```
<223> OTHER INFORMATION: Description of Artificial Sequence:synthetic
      peptide
<220> FEATURE:
<223> OTHER INFORMATION: Xaa at position 1 is an amino acid or if Xaa
      is not
<223> OTHER INFORMATION: present, a hydrogen will be attached to the
      adjacent
<223> OTHER INFORMATION: residue.
<220> FEATURE:
<223> OTHER INFORMATION: Xaa at position 5 may be Thr or Cys
<220> FEATURE:
<223> OTHER INFORMATION: Xaa at position 6 is an amino acid, or if Xaa
      is not
<223> OTHER INFORMATION: present, a hydrogen will be attached to the
      adjacent
<223> OTHER INFORMATION: residue.

<400> SEQUENCE: 1

Xaa Arg Gly Asp Xaa Xaa
 1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:synthetic
      peptide
<220> FEATURE:
<223> OTHER INFORMATION: Xaa at position 4 may be Ser, Thr, or Cys

<400> SEQUENCE: 2

Arg Gly Asp Xaa
 1

<210> SEQ ID NO 3
<211> LENGTH: 13
<212> TYPE: PRT
<213> ORGANISM: Artificial Sequence
<220> FEATURE:
<221> NAME/KEY: MOD_RES
<222> LOCATION: (11)
<223> OTHER INFORMATION: acetamidomethyl
<220> FEATURE:
<221> NAME/KEY: MOD_RES
<222> LOCATION: (13)
<223> OTHER INFORMATION: acetamidomethyl
<220> FEATURE:
<221> NAME/KEY: MOD_RES
<222> LOCATION: (13)
<223> OTHER INFORMATION: AMIDATION
<220> FEATURE:
<223> OTHER INFORMATION: Description of Artificial Sequence:synthetic
      peptide

<400> SEQUENCE: 3

Gly Arg Gly Asp Val Arg Gly Asp Phe Lys Cys Gly Cys
 1               5                  10

<210> SEQ ID NO 4
<211> LENGTH: 12
<212> TYPE: PRT
<213> ORGANISM: Artificial Sequence
<220> FEATURE:
<221> NAME/KEY: MOD_RES
<222> LOCATION: (10)
<223> OTHER INFORMATION: acetamidomethyl
<220> FEATURE:
<221> NAME/KEY: MOD_RES
<222> LOCATION: (12)
<223> OTHER INFORMATION: acetamidomethyl
<220> FEATURE:
<221> NAME/KEY: MOD_RES
```

```
<222> LOCATION: (12)
<223> OTHER INFORMATION: AMIDATION
<220> FEATURE:
<223> OTHER INFORMATION: Description of Artificial Sequence:synthetic
      peptide

<400> SEQUENCE: 4

Gly Arg Gly Asp Val Arg Gly Asp Phe Cys Gly Cys
  1               5                  10

<210> SEQ ID NO 5
<211> LENGTH: 15
<212> TYPE: PRT
<213> ORGANISM: Artificial Sequence
<220> FEATURE:
<221> NAME/KEY: MOD_RES
<222> LOCATION: (1)
<223> OTHER INFORMATION: acetamidomethyl
<220> FEATURE:
<221> NAME/KEY: MOD_RES
<222> LOCATION: (3)
<223> OTHER INFORMATION: acetamidomethyl
<220> FEATURE:
<223> OTHER INFORMATION: Description of Artificial Sequence:synthetic
      peptide

<400> SEQUENCE: 5

Cys Gly Cys Arg Arg Arg Arg Arg Arg Arg Arg Gly Asp Val
  1               5                  10                  15

<210> SEQ ID NO 6
<211> LENGTH: 15
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (13)
<223> OTHER INFORMATION: acetamidomethyl
<220> FEATURE:
<221> NAME/KEY: MOD_RES
<222> LOCATION: (15)
<223> OTHER INFORMATION: acetamidomethyl
<220> FEATURE:
<223> OTHER INFORMATION: Description of Artificial Sequence:synthetic
      peptide

<400> SEQUENCE: 6

Ser Tyr Gly Arg Gly Asp Val Arg Gly Asp Phe Lys Cys Gly Cys
  1               5                  10                  15

<210> SEQ ID NO 7
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence:synthetic
      peptide
```

```
<400> SEQUENCE: 7

Ser Tyr Gly Arg Gly Asp Val Arg Gly Asp Phe Lys Cys Thr Cys Cys
1               5                   10                  15

Ala

<210> SEQ ID NO 8
<211> LENGTH: 12
<212> TYPE: PRT
<213> ORGANISM: Artificial Sequence
<220> FEATURE:
<221> NAME/KEY: MOD_RES
<222> LOCATION: (10)
<223> OTHER INFORMATION: acetamidomethyl
<220> FEATURE:
<221> NAME/KEY: MOD_RES
<222> LOCATION: (12)
<223> OTHER INFORMATION: acetamidomethyl
<220> FEATURE:
<221> NAME/KEY: MOD_RES
<222> LOCATION: (12)
<223> OTHER INFORMATION: AMIDATION
<220> FEATURE:
<223> OTHER INFORMATION: Description of Artificial Sequence:synthetic
      peptide

<400> SEQUENCE: 8

Gly Arg Asp Gly Val Arg Gly Asp Phe Cys Gly Cys
1               5                   10
```

RADIOLABELED COMPOUNDS FOR THROMBUS IMAGING

This application is a divisional of allowed U.S. patent application Ser. No. 08/253,317, filed Jun. 3, 1994 and now U.S. Pat. No. 5,830,856, which is a continuation-in-part of U.S. patent application Ser. No. 08/044,825, filed Apr. 8, 1993 and now abandoned, which is a continuation-in part of U.S. patent application Ser. No. 07/653,012, filed Feb. 8, 1991 and now abandoned; this application is also a continuation-in part of allowed U.S. patent application Ser. No. 08/335,832, filed Jan. 5, 1995 and now U.S. Pat. No. 5,925,331, is a U.S. national phase application claiming priority to PCT/US93/04794, filed May 21, 1993.

BACKGROUND OF THE INVENTION

1. Field of the Invention

This invention relates to scintigraphic imaging agents and reagents, and methods for producing such agents and reagents. Specifically, the invention relates to reagents that can be radiolabeled with technetium-99m (Tc-99m), methods and kits for making and radiolabeling such reagents, and methods for using such radiolabeled reagents to image sites of thrombus formation in a mammalian body.

2. Description of the Prior Art

Thrombosis and thromboembolism, in particular deep vein thrombosis (DVT) and pulmonary embolism (PE), are common clinical conditions that are associated with significant morbidity and mortality. It has been estimated that in the U.S. approximately 5 million patients experience one or more episodes of DVT per year and that over 500,000 cases of pulmonary embolism occur, resulting in 100,000 deaths (J. Seabold, Society of Nuclear Medicine Annual Meeting 1990). It has also been estimated that over 90% of all pulmonary emboli arise from DVT in the lower extremities. Anticoagulant therapy can effectively treat these conditions if applied early enough. However, such treatment is associated with risks (e.g. internal bleeding) that prevent unnecessary prophylactic application. More advanced techniques of thrombolytic intervention (such as the administration of recombinant tissue plasminogen activator or streptokinase) can be used in acute cases, but these techniques carry even greater risk. Moreover, effective clinical application of these techniques requires that the site of the offending thrombus be identified so as to monitor the effect of treatment.

For these reasons, a rapid means of localizing thrombi in vivo, most preferably using non-invasive methods, is highly desirable. Methods currently utilized for the identification of sites of deep-vein thrombosis are contrast venography and compression B-mode ultrasound; the choice of which technique is used depends on the expected location of the thrombus. However, the former technique is invasive and both techniques are uncomfortable for the patient. In addition, these methods are in many cases either unsuitable or yield inaccurate results.

Current methods used to diagnose PE include chest X-ray, electrocardiogram (EKG), arterial oxygen tension, perfusion and ventilation lung scans, and pulmonary angiography. Apart from the latter (invasive) procedure, none of these methods is capable of providing an unequivocal diagnosis.

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

A variety of radionuclides are known to be useful for radioimaging, including $^{67}$Ga, $^{68}$Ga, $^{99m}$Tc (Tc-99m), $^{111}$In, $^{123}$I, and $^{169}$Ybe. Of these radionuclides, Tc-99m and $^{111}$In are preferred single photon-emitting radionuclides and $^{68}$Ga is preferred as a positron-emitting radionuclide. Tc-99m is a preferred radionuclide because it does not emit alpha or beta particle radiation and emits gamma radiation at about 140 keV, has a physical half-life of 6 hours, and is readily available on-site using a molybdenum-99/technetium-99m generator.

A gamma-emitting radiotracer that binds specifically to a component of a thrombus in preference to other tissues when administered in vivo can provide an external scintigraphic image which defines the location of the thrombus-bound radiotracer and hence the thrombus. Thrombi are constructs of blood cells (largely activated platelets) enmeshed in cross-linked fibrin. Activated platelets are particularly good targets for radioimaging thrombi because they are not normally found in circulating blood (which contains unactivated platelets).

Activated platelets express the GPIIb/IIIa receptor on their cell surfaces. The normal ligand for this receptor is fibrinogen (Plow et al., 1987, *Perspectives in Inflammation, Neoplasia and Vascular Cell Biology*, pp. 267–275). However, small, synthetic analogues, which may be but are not necessarily peptides, have been developed that bind to this receptor (examples include Klein et al., 1992, U.S. Pat. No. 5,086,069 and Egbertson et al., 1992, European Patent Application No. EPA 0478328A1). Although many of these synthetic molecules bind with only low affinity, others have been made that have very high affinity (see Egbertson et al., ibid.).

Attempts to provide radiotracers for imaging thrombi are known in the prior art. These include autologous platelets, labeled with either $^{111}$In or $^{99m}$Tc (Tc-99m), and $^{123}$I- and $^{125}$I-labeled fibrinogen (the latter detected with a gamma scintillation probe as opposed to a gamma camera). Additional radiolabeled compounds used to label thrombi include plasmin, plasminogen activators, heparin, fibronectin, fibrin Fragment $E_1$ and anti-fibrin and anti-platelet monoclonal antibodies (see Knight, 1990, *Sem. Nucl. Med.* 20: 52–67 for review).

Compounds having the ability to bind to the platelet GPIIb/IIIa receptor are known in the prior art.

Ruoslahti & Pierschbacher, U.S. Pat. No. 4,578,079 describe peptides of sequence X-Arg-Gly-Asp-R-Y (SEQ ID NO: 1), wherein X and Y are either H or an amino acid, and R is Thr or Cys, the peptides being capable of binding to platelets.

Ruoslahti & Pierschbacher, U.S. Pat. No. 4,792,525 describe peptides of sequence Arg-Gly-Asp-X (SEQ ID NO: 2), wherein X is Ser, Thr or Cys, the peptides being capable of binding to platelets.

Klein et al., 1992, U.S. Pat. No. 5,086,069 disclose guanine derivatives that bind to the GPIIb/IIIa receptor.

Pierschbacher et al., 1989, PCT/US88/04403 disclose conformationally-restricted RGD-containing peptides for inhibiting cell attachment to a substratum.

Nutt et al., 1990, European Patent Application 90202015.5 disclose cyclic RGD peptides that are fibrinogen receptor antagonists.

Nutt et al., 1990, European Patent Application 90202030.4 disclose cyclic RGD peptides that are fibrinogen receptor antagonists.

Nutt et al., 1990, European Patent Application 90202031.2 disclose cyclic RGD peptides that are fibrinogen receptor antagonists.

Nutt et al., 1990, European Patent Application 90202032.0 disclose cyclic RGD peptides that are fibrinogen receptor antagonists.

Nutt et al., 1990, European Patent Application 90311148.2 disclose cyclic peptides that are fibrinogen receptor antagonists.

Nutt et al., 1990, European Patent Application 90311151.6 disclose cyclic peptides that are fibrinogen receptor antagonists.

Ali et al., 1990, European Patent Application 90311537.6 disclose cyclic peptides that are fibrinogen receptor antagonists.

Barker et al., 1991, PCT/US90/03788 disclose cyclic peptides for inhibiting platelet aggregation.

Pierschbacher et al., 1991, PCT/US91/02356 disclose cyclic peptides that are fibrinogen receptor antagonists.

Duggan et al, 1992, European Patent Application 92304111.5 disclose fibrinogen receptor antagonists.

Garland et al, 1992 European Patent Applications 92103861.8 and 92108214.5 disclose phenylamide derivatives as platelet aggregation inhibitors.

Bondinell et al, 1993, International Patent Application Serial No. PCT/US92/05463 disclose bicyclic fibrinogen antagonists.

Blackburn et al., International Patent Application Serial No. PCT/US92/08788, disclose nonpeptidyl integrin inhibitors having specificity for the GPIIb/IIIa receptor.

Egbertson et al., 1992, European Patent Application 0478328A1 disclose tyrosine derivatives that bind with high affinity to the GPIIb/IIIa receptor.

Ojima et al., 1992, 204th Meeting, Amer. Chem. Soc. Abst. 44 disclose synthetic multimeric RDGF peptides useful in inhibiting platelet aggregation.

Hartman et al., 1992, *J. Med. Chem.* 35: 4640–4642 describe tyrosine derivatives that have a high affinity for the GPIIb/IIIa receptor.

Radiolabeled peptides for radioimaging thrombi have been reported in the prior art.

Stuttle, 1990, PCT/GB90/00933 discloses radioactively labeled peptides containing from 3 to 10 amino acids comprising the sequence arginine-glycine-aspartic acid (RGD), capable of binding to an RGD binding site in vivo.

Rodwell et al., 1991, PCT/US91/03116 disclose conjugates of "molecular recognition units" with "effector domains".

The use of chelating agents for radiolabeling peptides, and methods for labeling peptides with Tc-99m are known in the prior art and are disclosed in co-pending U.S. patent applications Ser. No. 07/653,012, now abandoned, which was allowed as U.S. Pat. No. 5,654,272; Ser. No. 07/807,062, now U.S. Pat. No. 5,443,815; Ser. Nos. 07/871,282; 07/886,752, now abandoned, which has been allowed as U.S. Pat. No. 5,736,122; Ser. No. 07/893,981, now U.S. Pat. No. 5,508,020; Ser. No. 07/955,466, now abandoned; Ser. No. 08/019,864, now U.S. Pat. No. 5,552,525; Ser. No. 08/073,577, now U.S. Pat. No. 5,561,220; Ser. No. 08/210,822, now abandoned; Ser. No. 08/236,402 and Ser. No. 08/241,625, now U.S. Pat. No. 5,783,170, and radiolabeled peptides for use as scintigraphic imaging agents for imaging thrombi are known in the prior art and are disclosed in co-pending U.S. patent applications Ser. Nos. 07/886,752, 07/893,981 and 08/044,825, which issued as U.S. Pat. No. 5,645,815 and International Patent Applications Serial Nos. PCT/US92/00757, PCT/US92/10716, PCT/US93/02320, PCT/US93/03687, PCT/US93/04794, PCT/US93/05372, PCT/US93/06029, PCT/US93/09387, PCT/US94/01894, PCT/US94/03878, and PCT/US94/05895, each of which are hereby incorporated by reference in its entirety.

There remains a need for small (to enhance blood and background tissue clearance), synthetic (to make routine manufacture practicable and to ease regulatory acceptance), high-affinity, specific-binding molecules radiolabeled with a convenient radiolabel, preferably Tc-99m, for use in imaging thrombi in vivo. Small synthetic compounds that bind specifically to the GPIIb/IIIa receptor on activated platelets, that are radiolabeled with a convenient radioisotope, preferably Tc-99m, $^{111}$In or $^{68}$Ga, fulfill this need in the art, and are provided by this invention.

SUMMARY OF THE INVENTION

This invention provides small, synthetic, radiolabeled (preferably Tc-99m, $^{111}$In or $^{68}$Ga labeled) compounds that bind to the GPIIb/IIIa receptor with high affinity, as scintigraphic agents for non-invasive imaging of thrombi in vivo. The invention thereby provides scintigraphic thrombus imaging agents that are radioactively-labeled reagents. Specifically, the invention provides reagents for preparing thrombus imaging agents that are radiolabeled with technetium-99m (Tc-99m), $^{111}$In or $^{68}$Ga, preferably with Tc-99m. The reagents of the invention are each comprised of a specific binding compound, including but not limited to peptides, that binds specifically and with high affinity to the platelet glycoprotein IIb/IIIa (GPIIa/IIIb) receptor, and is covalently linked to a radiolabel-complexing moiety.

We have found that, for optimal imaging, the reagent must be capable of binding to the platelet GPIIb/IIIa receptor with sufficient affinity that it inhibits the adenosine diphosphate (ADP)-induced aggregation of human platelets in a standard platelet aggregation assay (see Example 3 below) to the extent of 50% when present at a concentration of no more than 1 μM.

It is of distinct commercial advantage to use small compounds, preferably having a molecular weight of less than about 10,000 daltons. Such small compounds can be readily manufactured. Moreover, they are likely not to be immunogenic and to clear rapidly from the vasculature, thus allowing for better and more rapid imaging of thrombi. In contrast, larger molecules such as antibodies of fragments thereof, or other biologically-derived peptides larger than 10,000 daltons, are costly to manufacture, and are likely to be immunogenic and clear more slowly from the bloodstream, thereby interfering with rapid diagnoses of thrombi in vivo.

The invention also provides reagents wherein the specific binding compounds are linear or cyclic peptides having an amino acid sequence of 4 to 100 amino acids and a molecular weight no greater than about 10,000 daltons.

One aspect of the invention provides a reagent for preparing a thrombus imaging agent that is capable of being radiolabeled for imaging thrombi within a mammalian body, comprising a specific binding compound that specifically binds to the platelet GPIIb/IIIa receptor, and that is covalently linked to a Tc-99m complexing moiety of formula:

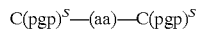

wherein $C(pgp)^S$ is a protected cysteine and (aa) is any primary α- or β-amino acid not containing a thiol group. In a preferred embodiment, the amino acid is glycine.

In another embodiment, the invention provides a reagent for preparing a thrombus imaging agent that is capable of being radiolabeled for imaging thrombi within a mammalian body, comprising a specific binding compound that specifically binds to the platelet GPIIb/IIIa receptor, that is covalently linked to a Tc-99m complexing moiety comprising a single thiol-containing moiety of formula:

$$A-CZ(B)-\{(C(R^1R^2)\}_n-X \qquad \text{II.}$$

wherein A is H, HOOC, H$_2$NOC, (amino acid or peptide)-NHOC, (amino acid or peptide)-OOC or R$^4$; B is H, SH or —NHR$^3$, —N(R$^3$)-(amino acid or peptide) or R$^4$; Z is H or R$^4$; X is SH or —NHR$^3$, —N(R$^3$)-(amino acid or peptide) or R$^4$; R$^1$, R$^2$, R$^3$ and R$^4$ are independently H or straight or branched chain or cyclic lower alkyl; n is 0, 1 or 2; wherein (peptide) is a peptide of 2 to about 10 amino acids; and: (1) where B is —NHR$^3$ or —N(R$^3$)-(amino acid or peptide), X is SH and n is 1 or 2; (2) where X is —NHR$^3$ or —N(R$^3$)-(amino acid or peptide), B is SH and n is 1 or 2; (3) where B is H or R$^4$, A is HOOC, H$_2$NOC, (amino acid or peptide)-NHOC, (amino acid or peptide)-OOC, X is SH and n is 0 or 1; (4) where A is H or R$^4$, then where B is SH, X is —NHR$^3$ or —N(R$^3$)-(amino acid or peptide) and where X is SH, B is —NHR$^3$ or —N(R$^3$)-(amino acid or peptide); (5) where X is H or R$^4$, A is HOOC, H$_2$NOC, (amino acid or peptide)-NHOC, (amino acid or peptide)-OOC and B is SH; (6) where Z is methyl, X is methyl, A is HOOC, H$_2$NOC, (amino acid or peptide)-NHOC, (amino acid or peptide)-OOC and B is SH and n is 0; and wherein the thiol moiety is in the reduced form and wherein (amino acid) is any primary α- or β-amino acid not containing a thiol group.

In particular embodiments of this aspect of the invention, the radiolabel-complexing moiety has a formula that is:

IIa. -(amino acid)$^1$-(amino acid)$^2$\{A—CZ(B)—\{C(R$^1$R$^2$)\}$_n$—X\},

IIb. -\{A—CZ(B)—\{C(R$^1$R$^2$(\}$_n$—X\}-(amino acid)$^1$-(amino acid)$^2$,

IIc. -(a primary α,ω- or β,ω-diamino acid)-(amino acid)$^1$-\{A—CZ(B)—\{C(R$^1$R$^2$)\}$_n$—X\}, or IId. -\{A—CZ(B)—\{C(R$^1$R$^2$)\}$_n$—X\}-(amino acid)$^1$-(a primary α,ω- or β,ω-diamino acid)

wherein (amino acid)$^1$ and (amino acid)$^2$ are each independently any naturally-occurring, modified, substituted or altered α- or β-amino acid not containing a thiol group; A is H, HOOC, H$_2$NOC, (amino acid or peptide)-NHOC, (amino acid or peptide)-OOC or R$^4$; B is H, SH or —NHR$^3$, —N(R$^3$)-(amino acid or peptide) or R$^4$; Z is H or R$^4$; X is SH or —NHR$^3$, —N(R$^3$)-(amino acid or peptide) or R$^4$; R$^1$, R$^2$, R$^3$ and R$^4$ are independently H or straight or branched chain or cyclic lower alkyl; n is an integer that is either 0, 1 or 2; (peptide) is a peptide of 2 to about 10 amino acids; and: (1) where B is —NHR or —N(R 3)-(amino acid or peptide), X is SH and n is 1 or 2; (2) where X is —NHR or —N(R$^3$)-(amino acid or peptide), B is SH and n is 1 or 2; (3) where B is H or R$^4$, A is HOOC, H$_2$NOC, (amino acid or peptide)-NHOC, (amino acid or peptide)-OOC, X is SH and n is 0 or 1; (4) where A is H or R$^4$, then where B is SH, X is —NHR$^3$ or —N(R$^3$)-(amino acid or peptide) and where X is SH, B is —NHR$^3$ or —N(R$^3$)-(amino acid or peptide); (5) where X is H or R$^4$, A is HOOC, H$_2$NOC, (amino acid or peptide)-NHOC, (amino acid or peptide)-OOC and B is SH; (6) where Z is methyl, X is methyl, A is HOOC, H$_2$NOC, (amino acid or peptide)-NHOC, (amino acid or peptide)-OOC and B is SH and n is 0; and wherein the thiol group is in the reduced form.

In another embodiment, the invention provides a reagent for preparing a thrombus imaging agent that is capable of being radiolabeled for imaging thrombi within a mammalian body, comprising a specific binding compound that specifically binds to the platelet GPIIb/IIIa receptor, and that is covalently linked to a radiolabel-complexing moiety of formula:

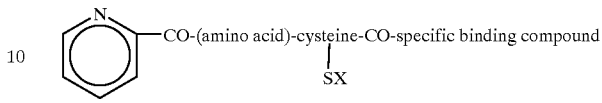

(for purposes of this invention, radiolabel-binding moieties having this structure will be referred to as picolinic acid (Pic)-based moieties); or specific binding compound

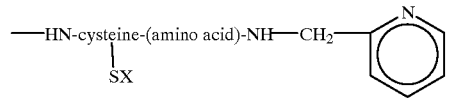

(for purposes of this invention, radiolabel-binding moieties having this structure will be referred to as picolylamine (Pica)-based moieties); wherein X is H or a protecting group; (amino acid) is any primary α- or β-amino acid not containing a thiol group; the radiolabel-complexing moiety is covalently linked to the specific binding compound and the complex of the radiolabel-complexing moiety and the radiolabel is electrically neutral. In a preferred embodiment, the amino acid is glycine and X is an acetamidomethyl protecting group. In additional preferred embodiments, the specific binding compound is covalently linked to the radiolabel-complexing moiety via an amino acid, most preferably glycine.

Yet another embodiment of the invention provides a reagent for preparing a thrombus imaging agent that is capable of being radiolabeled for imaging thrombi within a mammalian body, comprising a specific binding compound that specifically binds to the platelet GPIIb/IIIa receptor, and that is covalently linked to a radiolabel-complexing moiety that is a bisamino bisthiol radiolabel-complexing moiety. The bisamino bisthiol moiety in this embodiment of the invention has a formula selected from the group consisting of:

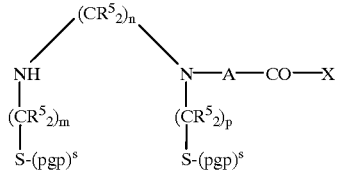

wherein each R$^5$ can be independently H, CH$_3$ or C$_2$H$_5$; each (pgp)$^s$ can be independently a thiol protecting group or H; m, n and p are independently 2 or 3; A is linear or cyclic lower alkyl, aryl, heterocyclyl, combinations or substituted derivatives thereof; and X is a specific binding compound; and

VI.

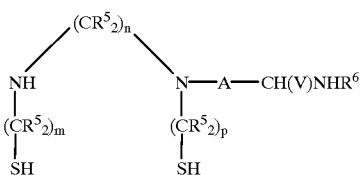

wherein each $R^5$ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or CO-(amino acid or peptide); $R^6$ is H, (amino acid) or peptide or a specific binding compound; provided that when V is H, $R^6$ is amino acid or peptide or a specific binding compound and when $R^6$ is H, V is amino acid or peptide or a specific binding compound, wherein (amino acid) is any primary α- or β-amino acid not containing a thiol group. (For purposes of this invention, radiolabel-binding moieties having these structures will be referred to as "BAT" moieties). In a preferred embodiment, the specific binding compound is covalently linked to the radiolabel-complexing moiety via an amino acid, most preferably glycine.

In preferred embodiments of the aforementioned aspects of this invention, the specific binding compound is a peptide is comprised of between 4 and 100 amino acids. The most preferred embodiment of the radiolabel is technetium-99m.

The reagents of the invention may be formed wherein the specific binding compounds or the radiolabel-complexing moieties are covalently linked to a polyvalent linking moiety. Polyvalent linking moieties of the invention are comprised of at least 2 identical linker functional groups capable of covalently bonding to specific binding compounds or radiolabel-complexing moieties. Preferred linker functional groups are primary or secondary amines, hydroxyl groups, carboxylic acid groups or thiol-reactive groups. In preferred embodiments, the polyvalent linking moieties are comprised of bis-succinimidylmethylether (BSME), 4-(2,2-dimethylacetyl)benzoic acid (DMAB), tris(succinimidylethyl)amine (TSEA), tris(acetamidoethyl)amine, bis-(acetamidoethyl)ether, bis-(acetamidomethyl) ether, N-{2-(N',N'-bis(2-succinimidoethyl)aminoethyl)}-$N^6,N^9$-bis(2-methyl-2-mercaptopropyl)-6,9-diazanonanamide (BAT-BS), α,ε-bisacetyllysine, lysine and 1,8-bis-acetamido-3,6-dioxa-octane.

The invention also comprises scintigraphic imaging agents that are complexes of the reagents of the invention with Tc-99m, $^{111}$In or $^{68}$Ga, most preferably Tc-99m and methods for radiolabeling the reagents of the invention to provide such scintigraphic imaging agents. Tc-99m radiolabeled complexes provided by the invention are formed by reacting the reagents of the invention with Tc-99m in the presence of a reducing agent. Preferred reducing agents include but are not limited to dithionite ion, stannous ion and ferrous ion. Complexes of the invention are also formed by labeling the reagents of the invention with Tc-99m by ligand exchange of a prereduced Tc-99m complex as provided herein.

The invention also provides kits for preparing scintigraphic imaging that are the reagents of the invention radiolabeled with Tc-99m. Kits for labeling the reagents provided by the invention with Tc-99m are comprised of a sealed vial containing a predetermined quantity of a reagent of the invention and a sufficient amount of reducing agent to label the reagent with Tc-99m.

This invention provides methods for preparing peptide reagents of the invention by chemical synthesis in vitro. In a preferred embodiment, peptides are synthesized by solid phase peptide synthesis.

This invention provides methods for using scintigraphic imaging agents that are Tc-99m labeled reagents for imaging thrombi within a mammalian body by obtaining in vivo gamma scintigraphic images. These methods comprise administering an effective diagnostic amount of Tc-99m labeled reagents of the invention and detecting the gamma radiation emitted by the Tc-99m label localized at the thrombus site within the mammalian body.

Specific preferred embodiments of the present invention will become evident from the following more detailed description of certain preferred embodiments and the claims.

DETAILED DESCRIPTION OF THE INVENTION

Figure 1:
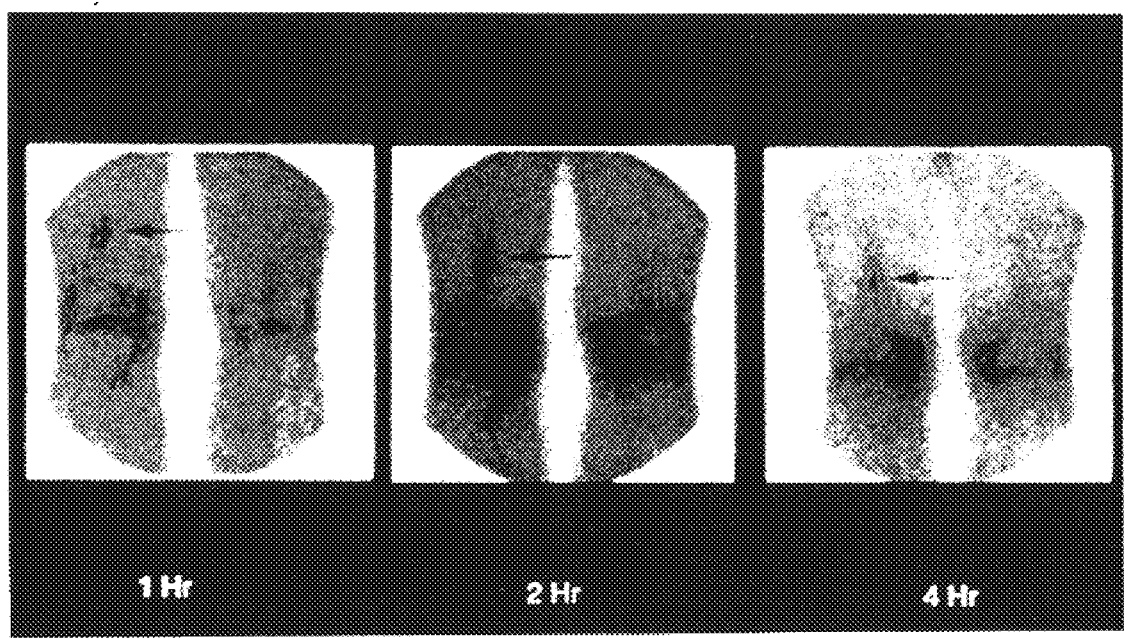
FIG. 1 illustrates scintigraphic imaging of deep-vein thrombi in the thigh in human patients using a Tc-99m radiolabel peptide reagent of the invention.

The present invention provides reagents, including peptide reagents, for preparing radiolabeled thrombus imaging agents for imaging a thrombus within a mammalian body. The reagents provided by the invention comprise a radiolabel binding moiety covalently linked to a specific binding compound that binds a platelet receptor that is the platelet GPIIb/IIIa receptor and is capable of inhibiting human platelet aggregation in platelet-rich plasma by 50% when present at a concentration of no more than 1 μM (i.e., $IC_{50}$=1 μM). For purposes of the invention, the term thrombus imaging reagent will refer to embodiments of the invention comprising a specific binding compound covalently linked to a radiolabel-complexing moiety and radiolabeled, preferably with Tc-99m, $^{111}$In or $^{68}$Ga, most preferably with Tc-99m.

We have previously found that, for optimal imaging, a reagent as disclosed herein must be capable of binding to platelet glycoprotein IIb/IIIa receptor with sufficient affinity that it inhibits adenosine diphosphate (ADP)-induced platelet aggregation in a standard assay (see Example 3) when present at concentrations up to 0.3 μM ($IC_{50}$≦0.3 μM). This invention was disclosed in U.S. patent application Ser. No. 08/044,825, now abandoned, which issued as U.S. Pat. No. 5,645,815, and International Patent Application Serial No. PCT/US9403878, the disclosures of both incorporated by reference in their entireties).

We have now found that advantageously high-quality in vivo scintigraphic images may be obtained using a radiolabeled scintigraphic imaging agent as disclosed herein having an $IC_{50}$≦1 μM. We have found that a dimeric reagent of the invention (P280) having an $IC_{50}$ of 0.087 μM when unlabeled was converted to its monomeric counterpart (P246) when labeled with Tc-99m as described herein. This Tc-99m labeled reagent was found to yield excellent scintigraphic images of venous thrombi in an in vivo canine model system and of deep-vein thrombi in humans in vivo. When the monomer was assayed for platelet aggregation inhibition, the $IC_{50}$ value was found to be 0.85 μM. Thus, these results indicate that embodiments of the reagents of the invention having $IC_{50}$ values of up to about 1 μM are useful as efficacious scintigraphic imaging agents.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Another advantage of the present invention is that none of the preferred radionuclides (Tc-99m, Ga-67, In-111) are toxic, in contrast to other radionuclides known in the art (for example, $^{125}$I.

In the Tc-99m complexing moieties and compounds covalently linked to such moieties that contain a thiol covalently linked to a thiol protecting group { (pgp)$^S$} provided by the invention, the thiol-protecting groups may be the same or different and may be but are not limited to:

—CH$_2$-aryl (aryl is phenyl or alkyl or alkyloxy substituted phenyl);

—CH-(aryl)$_2$, (aryl is phenyl or alkyl or alkyloxy substituted phenyl);

—C-(aryl)$_3$, (aryl is phenyl or alkyl or alkyloxy substituted phenyl);

—CH$_2$-(4-methoxyphenyl);

—CH-(4-pyridyl)(phenyl)$_2$;

C(CH$_3$)$_3$

—9-phenylfluorenyl;

—CH$_2$NHCOR (R is unsubstituted or substituted alkyl or aryl);

—CH$_2$—NHCOOR (R is unsubstituted or substituted alkyl or aryl);

—CONHR (R is unsubstituted or substituted alkyl or aryl);

—CH$_2$—S—CH$_2$-phenyl

Preferred protecting groups have the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

Each specific-binding peptide-containing embodiment of the invention is comprised of a sequence of amino acids. The term amino acid as used in this invention is intended to include all L- and D-, primary α- or β-amino acids, naturally occurring and otherwise. Specific-binding peptides provided by the invention include but are not limited to peptides having the following sequences (the amino acids in the following peptides are L-amino acids except where otherwise indicated):

CH$_2$CO.Y$_D$.Apc.GDCGGG

CH$_2$CO.Y$_D$.Apc.GDCKG

CH$_2$CO.Y$_D$.Apc.GDCGG

CH$_2$CO.Y$_D$.Apc.GDC

CH$_2$CO.Y$_D$.Apc.GDCK

CH$_2$CO.Y$_D$.Amp.GDC

CH$_2$CO.Y$_D$.Amp.GDCK and

O-(4-piperidinyl)butyl tyrosine.

Specific-binding peptides of the present invention can be chemically synthesized in vitro. Peptides of the present invention can generally advantageously be prepared on an peptide synthesizer. The peptides of this invention can be synthesized wherein the radiolabel-binding moiety is covalently linked to the peptide during chemical synthesis in vitro, using techniques well known to those with skill in the art. Such peptides covalently linked to the radiolabel-binding moiety during synthesis are advantageous because specific sites of covalent linkage can be determined.

Radiolabel binding moieties of the invention may be introduced into the target specific peptide during peptide synthesis. For embodiments comprising picolinic acid {(Pic-); e.g., Pic-Gly-Cys(protecting group)-}, the radiolabel-binding moiety can be synthesized as the last (i.e., amino-terminal) residue in the synthesis. In addition, the picolinic acid-containing radiolabel-binding moiety may be covalently linked to the ε-amino group of lysine to give, for example, αN(Fmoc)-Lys-εN{Pic-Gly-Cys (protecting group)}, which may be incorporated at any position in the peptide chain. This sequence is particularly advantageous as it affords an easy mode of incorporation into the target binding peptide.

Similarly, the picolylamine (Pica)-containing radiolabel-binding moiety {-Cys(protecting group)-Gly-Pica} can be prepared during peptide synthesis by including the sequence {-Cys(Cys(protecting group)-Gly-} at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

Examples of small synthetic peptides containing the Pic-Gly-Cys- and -Cys-Gly-Pica chelators are provided in the Examples hereinbelow. This invention provides for the incorporation of these chelators into virtually any peptide capable of specifically binding to a thrombus in vivo, resulting in a radiolabeled peptide having Tc-99m held as neutral complex.

This invention also provides specific-binding small synthetic peptides which incorporate bisamine bisthiol (BAT) chelators which may be labeled with Tc-99m. This invention provides for the incorporation of these chelators into virtually any peptide capable of specifically binding to a thrombus in vivo, resulting in a radiolabeled peptide having Tc-99m held as neutral complex. An example of a small synthetic peptide containing a BAT chelator as radiolabel-binding moiety is provided in the Examples hereinbelow.

In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a reagent of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts. In a preferred embodiment of the invention, a kit for preparing technetium-labelled reagents is provided. An appropriate amount of the reagent is introduced into a vial containing a reducing agent, such as stannous chloride, in an amount sufficient to label the reagent with Tc-99m. An appropriate amount of a transfer ligand as described (such as tartrate, citrate, gluconate or mannitol, for example) can also be included. The kit may also contain conventional pharmaceutical adjunct materials such as, for example, pharmaceutically acceptable salts to adjust the osmotic pressure, buffers, preservatives and the like. The components of the kit may be in liquid, frozen or dry form. In a preferred embodiment, kit components are provided in lyophilized form.

Radiolabeled thrombus imaging reagents according to the present invention may be prepared by the addition of an appropriate amount of Tc-99m or Tc-99m complex into the vials and reaction under conditions described in Example 4 hereinbelow.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

The thrombus imaging reagents provided by the present invention can be used for visualizing thrombi in a mammalian body when Tc-99m labeled. In accordance with this invention, the Tc-99m labeled reagents are administered in a single unit injectable dose. The Tc-99m labeled reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging of the thrombus in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

It will also be recognized by those having skill in the relevant arts that thrombi are commonly found at sites of atherosclerotic plaque; that integrin receptors that may bind to the scintigraphic imaging agents of the invention may be found in certain tumors; and that such integrin receptors are involved in cell adhesion processes that accompany or initiate leukocyte localization at sites of infection. Therefore it will be recognized that the scintigraphic imaging agents of this invention have additional utility as imaging agents for imaging sites in which the GPIIb/IIIa receptor is expressed, including atherosclerotic plaques, tumors and sites of infection.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzotriazol-1-yl)-1,1,3,3-tetramethyluronium hexafluorophosphate/hydroxybenzotriazole (HBTU/HOBT), and using p-hydroxymethylphenoxymethylpolystyrene (HMP) resin for carboxyl-terminus acids or Rink amide resin for carboxyl-terminus amides. Resin-bound products were routinely cleaved using a solution comprised of trifluoroacetic acid or 50/50 trifluoroacetic acid/dichloromethane, optionally containing water, thioanisole, ethanedithiol, and triethylsilane, prepared in ratios of 100:5:5:2.5:2 for 1.5–3 h at room temperature.

Where appropriate, N-terminal acetyl groups were introduced by treating the free N-terminal amino peptide bound to the resin with 20% v/v acetic anhydride in NMP (N-methylpyrrolidinone) for 30 min. For preparing branched-chain peptide reagents involving peptide chain synthesis from both the α- and ε-amines of lysine, Nα(Fmoc)Nε(Fmoc)-lysine was used during SPPS. Where appropriate, 2-chloroacetyl and 2-bromoacetyl groups were introduced either by using the appropriate 2-halo-acetic acid as the last residue to be coupled during SPPS or by treating the N-terminus free amino peptide bound to the resin with either 2-halo-acetic acid/diisopropylcarbodiimide/N-hydroxysuccinimide in NMP or 2-halo-acetic anhydride/diisopropylethylamine in NMP. Where appropriate, HPLC-purified 2-haloacetylated peptides were cyclized by stirring in a 0.1–1.0 mg/mL solution at pH8 optionally containing phosphate, bicarbonate or 0.5–1.0 mM EDTA for 0.5–48 hours, followed by acidification with acetic acid, lyophilization and HPLC purification. Where appropriate, Cys-Cys disulfide bond cyclizations were performed by treating the precursor cysteine-free thiol peptides at 0.1mg/mL in pH 7 buffer with aliquots of 0.006 M $K_3Fe(CN)_6$ until a stable yellow color persisted. The excess oxidant was reduced with excess cysteine, the mixture was lyophilized and then purified by HPLC.

Where appropriate, peptide thiol-chloroacetyl derived sulfides were prepared by reacting single thiol-containing peptides at a concentration of 2 to 50 mg/mL in water and acetonitrile or THF or DMF at pH 10 with the appropriate number (e.g., 0.5 molar equivalents for preparing dimers and 0.33 molar equivalents for preparing trimers) of the chloroacetyl polyvalent linker moiety for 0.5 to 24 hours. The solution was then neutralized with acetic acid, evaporated to dryness, and, if necessary, deprotected using 10 mL TFA and scavengers such as 0.2 mL triethylsilane for 30 to 90 minutes. The solution was concentrated and the product was precipitated with ether. Products were purified by preparative HPLC.

Where appropriate, BSME adducts were prepared by reacting single thiol-containing peptides (5 to 50 mg/mL in 50 mM sodium phosphate buffer, pH 7 to 8) with 0.5 molar equivalents of BMME (bis-maleimidomethylether) predissolved in acetonitrile at room temperature for approximately 1–18 hours. The solution was concentrated and the product was purified by HPLC.

Where appropriate, TSEA adducts were prepared by reacting single thiol-containing peptide (at concentrations of 10 to 100 mg/mL peptide in DMF, or 5 to 50 mg/mL peptide in 50 mM sodium phosphate (pH 8)/acetonitrile or THF) with 0.33 molar equivalents of TMEA (tris(2-maleimidoethyl)amine; as disclosed in U.S. Ser. No. 08/044,825, incorporated by reference) pre-dissolved in acetonitrile or DMF, with or without 1 molar equivalent of triethanolamine, at room temperature for approximately 1–18 h. Such reaction mixtures containing adducts were concentrated and the adducts were then purified using HPLC.

Where appropriate, BAT-BS adducts were prepared by reacting single thiol-containing peptide (at concentrations of 2 to 50 mg/mL peptide in 50 mM sodium phosphate (pH 8)/acetonitrile or THF) with 0.5 molar equivalents of BAT-BM (N-{2-(N'N'-bis(2-maleimido-ethyl)aminoethyl)}-N$^9$-(t-butoxycarbonyl)-N$^6$,N$^9$-bis(2-methyl-2-triphenylmethylthiopropyl)-6,9-diazanonanamide; as disclosed in U.S. Ser. No. 08/044,825, incorporated by reference) pre-dissolved in acetonitrile or THF, at room temperature for approximately 1–18 h. The solution was then evaporated to dryness and (BAT-BS)-peptide conjugates deprotected by treatment with 10 mL TFA and 0.2 mL triethylsilane for 1 h. The solution was concentrated, the product adducts precipitated with ether, and then purified by HPLC.

Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS) or electrospray mass spectroscopy (ESMS).

EXAMPLE 2

A General Method for Radiolabeling with Tc-99m

A 0.1 mg sample of a peptide reagent prepared as in Example 2 was dissolved in 0.1 mL of water, 50 mM potassium phosphate buffer, 0.1 M bicarbonate buffer or 10% hydroxypropylcyclodextrin (HPCD), each buffer at pH of 5–10. Tc-99m gluceptate was prepared by reconstituting a Glucoscan vial (E.I. DuPont de Nemours, Inc., Wilmington, Del.) with 1.0 mL of Tc-99m sodium pertechnetate containing up to 200 mCi and allowed to stand for 15 minutes at room temperature. 25 $\mu$L of Tc-99m gluceptate was then added to the peptide and the reaction allowed to proceed at room temperature or at 100° C. for 5–30 min and then filtered through a 0.2 $\mu$m filter.

The Tc-99m labeled peptide purity was determined by HPLC using the following conditions: a Waters DeltaPure RP-18, 5 $\mu$, 150 mm×3.9 mm analytical column was loaded with each radiolabeled peptide and the peptides eluted at a solvent flow rate equal to 1 mL/min. Gradient elution was performed beginning with 10% solvent A (0.1% CF3COOH/ H$_2$O) to 40% solvent B$_{90}$ (0.1 % CF$_3$COOH/90% CH$_3$CN/ H$_2$O) over the course of 20 min. The Tc-99m labeled peptide purity was determined by HPLC using the conditions described in the Footnotes in Table I. Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 1 using the method described herein.

TABLE I

| Peptides | FABMS MH$^+$ | Radiochemical Yield(%)* | HPLC R$_T$(min)** |
|---|---|---|---|
| CH$_2$CO.Y$_{DRGDC}$C$_{Acm}$GC$_{Acm}$amide[b] | 1057 | 97[2] | 10.0, 10.4, 10.6[2] |
| CH$_2$CO.Y$_D$RGDCGGC$_{Acm}$GC$_{Acm}$amide | 1171 | 99[2] | 13.5[2] |
| CH$_2$CO.Y$_D$.Apc.GDCGGGC$_{Acm}$GC$_{Acm}$amide | 1233 | 100[4] | 17.1, 18.1[2] |
| GRGDVRGDFKC$_{Acm}$GC$_{Acm}$amide(SEQ ID NO:3) | 1510 | 97[2] | 16.2, 16.8[2] |
| GRGDVRGDFC$_{Acm}$GC$_{Acm}$amide(SEQ ID NO:4) | 1382 | 94[2] | 16.4[2] |
| CH$_2$CO.Y$_D$Apc.GDCGGC$_{Acm}$GC$_{Acm}$GGF$_D$PRPG.NH$_2$ | 1845 | 90[4] | 16.6, 16.9[2] |
| (CH$_2$CO.Y$_D$Apc.GDCGGC$_{Acm}$GC$_{Acm}$GGC.amide)$_2$-BSME | 3020[a] | 98[4] | 9.3[2] |
| (CH$_2$CO.Y$_D$.Apc.GDCGGC$_{Acm}$GC$_{Acm}$GGC.amide)$_3$-TSEA | 4596 | 99[4] | 9.2, 11.6[5] |
| (CH$_2$CO.Y$_D$Apc.GDCGGC$_{Acm}$GC$_{Acm}$GGC.amide)$_2$-(BAT-BS) | 3409[a] | 98[3] | 10.3[5] |
| C$_{Acm}$GC$_{Acm}$RRRRRRRRRGDV(SEQ ID NO:5) | 2100 | 100[2] | 2.4[3]*** |
| (CH$_2$CO.Y$_D$Apc.GDCKGC$_{Acm}$GC$_{Acm}$GGC.amide)$_2$-BSME | 3163[a] | 98[4] | 9.6[5] |
| (CH$_2$COY$_D$.Amp.GDCGGC$_{Acm}$GC$_{Acm}$GGCamide)$_2$-(CH$_2$CO)$_2$K(N$\epsilon$-K)GCamide | 3357[a] | 99[8] | 4.6[6] |

TABLE I-continued

| | | | |
|---|---|---|---|
| (CH₂COY_D.Amp.GDCKGCGamide)₂-(CH₂CO)₂K(Nε-K)GCamide | 2573[a] | 99[8] | 4.8[6] |
| (CH₂COY_D.Apc.GDCGGC_Acm GC_Acm GGCamide)₂(CH₂CO)₂-K(Nε-K)GCamide | 3298[a] | 96[3] | 12.0[4] |

*Superscripts refer to the following labeling conditions:
1. The peptide was dissolved in 50 mM potassium phosphate buffer (pH 7.4) and labeled at room temperature.
2. The peptide was dissolved in 50 mM potassium phosphate buffer (pH 7.4) and labeled at 100° C.
3. The peptide was dissolved in water and labeled at room temperature.
4. The peptide was dissolved in water and labeled at 100° C.
5. The peptide was dissolved in 50 mM potassium phosphate buffer (pH 6.0) and labeled at 100° C.
6. The peptide was dissolved in 50 mM potassium phosphate buffer (pH 5.0) and labeled at room temperature.
7. The peptide was dissolved in a 50:50 mixture of ethanol/water and labeled at 100° C.
8. The peptide was dissolved in 0.9% sodium chloride solution and labeled at room temperature.
**HPLC methods (indicated by superscript after RT):
general:  solvent A =         0.1% CF₃COOH/H₂O
          solvent B₇₀ =       0.1% CF₃COOH/70% CH₃CN/H₂O
          solvent B₉₀ =       0.1% CF₃COOH/90% CH₃CN/H₂O
          solvent flow rate = 1 mL/min
Vydak column = Vydak 218TP54 RP-18, 5 μm, 220 mm x 4.6 mm analytical column with guard column
Brownlee column = Brownlee Spheri-5 RP-18, 5 μm, 220 mm x 4.6 mm column
Waters column = Waters Delta-Pak C18, 5 μm, 150 mm x 3.9 mm column
Waters column 2 = Waters Nova-Pak C18, 5μm, 100 mm x 8 mm radial compression column
Method 1: Brownlee column  100% A to 100% B₇₀ in 10 min
Method 2: Vydak column     100% A to 100% B₉₀ in 10 min
Method 3: Vydak column     100% A to 100% B₇₀ in 10 min
Method 4: Waters column    100% A to 100% B₉₀ in 20 min
Method 5: Waters column    100% A to 100% B₉₀ in 10 min
Method 6: Waters 2 column  100% A to 100% B₉₀ in 10 min
***Confirmed by sodium dodecyl sulfate-polyacrylamide gel electrophoresis
Single-letter abbreviations for amino acids can be found in G. Zubay, Biochemistry (2d. ed.), 1988 (MacMillen Publishing: New York) p.33; underlining indicates the formation of a thiol linkage between the linked amino acids of derivative groups; peptides are linked to BSH, ETAC, BSME, TSEA, (BAT-BS) or (CH₂CO)-containing linkers via the free thiol moiety of the unprotected cysteine residue (C) in each peptide; Ac = acetyl; Bz = benzoyl; Pic = picolinoyl (pyridine-2-carbonyl); Acm = acetamidomethyl; Mob = 4-methoxybenzyl; Apc = L-(S-(3-aminopropyl)cysteine); Hly = homolysine; FD = D-phenylalanine; YD = D-tyrosine; ma = 2-mercaptoacetic acid; mmp = 2-mercapto-2-methylpropionic acid; BAT = $N^6,N^9$-bis(2-mercapto-2-methylpropyl)-6,9-diazanonanoic acid; ETAC = 4-(O-CH₂CO-Gly-Gly-Cys.amide)acetophenone; BAT-BS = N-{2-N',N'-bis(2-succinimidoethyl) aminoethyl }-$N^6,N^9$-bis(2-mercapto-2-methylpropyl)-6,9-diazanonanamide; BSME = bis-succinimidomethylether; TSEA = tris-(2-succinimidoethyl)amine; NES = N-ethylsuccinimide; .BSH = 1,6-bis-succinimidohexane; Amp = 4-amidinophenylalanine
[a] = confirmed by electrospray mass spectrometry (ESMS)

EXAMPLE 3

Platelet Aggregation Inhibition Assays

Platelet aggregation studies were performed essentially as described by Zucker (1989, Methods in Enzymol. 169: 117–133). Briefly, platelet aggregation was assayed with or without putative platelet aggregation inhibitory compounds using fresh human platelet-rich plasma, comprising 300,000 platelets per microliter. Platelet aggregation was induced by the addition of a solution of adenosine diphosphate to a final concentration of 10 to 15 micromolar, and the extent of platelet aggregation monitored using a Bio/Data aggregometer (Bio/Data Corp., Horsham, Pa.). The concentrations of platelet aggregation inhibitory compounds used were varied from 0.1 to 500 μg/mL. The concentration of inhibitor that reduced the extent of platelet aggregation by 50% (defined as the IC$_{50}$) was determined from plots of inhibitor concentration versus extent of platelet aggregation. An inhibition curve for peptide RGDS was determined for each batch of platelets tested.

The results of these experiments are shown in Table II. In Table II, the compounds tested are as follows (RGDS is given as a positive control):

P47=AcSYGRGDVRGDFKC$_{Acm}$GC$_{Acm}$ (SEQ ID NO: 6)

P97=GRGDVRGDFKC$_{Acm}$GC$_{Acm}$amide (SEQ ID NO: 3)

P32=C$_{Acm}$GC$_{Acm}$RRRRRRRRRGDV (SEQ ID NO: 5)

P143=CH₂CO—Y$_D$RGDCGGC$_{Acm}$GC$_{Acm}$amide

P245=CH₂CO—Y$_D$.Apc.GDCGGC$_{Acm}$GC$_{Acm}$GGF$_D$PRPGamide

P63=AcSYGRGDVRGDFKCTCCA (SEQ ID NO: 7)

P98=GRDGVRGDFC$_{Acm}$GC$_{Acm}$amide(SEQ ID NO: 8)

P81=CH₂CO—Y$_D$RGDCC$_{Acm}$GC$_{Acm}$amide

P154=CH₂CO—Y$_D$ApcGDCGGGC$_{Am}$GC$_{Acm}$amide

P381=(CH₂CO—Y$_D$ApcGDCKGC$_{Acm}$GC$_{Acm}$GGC-amide)₂-BSME

P317=(CH₂CO—Y$_D$ApcGDCGGC$_{Acm}$GC$_{Acm}$GGC-amide)₃-TSEA

P246=CH₂CO—Y$_D$ApcGDCGGC$_{Acm}$GC$_{Acm}$GGC-amide

P357=(CH₂CO—Y$_D$ApcGDCGGC$_{Acm}$GC$_{Acm}$GGC-amide)₂-(BAT-BS)

P667=(CH₂COY$_D$.Apc.GDCGGC$_{Acm}$GC$_{Acm}$GGC-amide)₂(CH₂CO)₂K(Nε-K)GCamide

P747=(CH₂COY$_D$.Amp.GDCGGC$_{Acm}$GC$_{Acm}$GGC-amide)₂(CH₂CO)₂K(Nε-K)GCamide

P748=(CH₂COY$_D$.Amp.GDCKGCGamide)₂(CH₂CO)₂-K(Nε-K)GCamide (Single-letter abbreviations for amino acids can be found in G. Zubay, Biochemistry (2d. ed.), 1988 (MacMillen Publishing: New York) p.33; Ac=acetyl; Acm=acetamidomethyl; Apc=L-(S-(3-aminopropyl)cysteine); $Y_D$=D-tyrosine; BSME=bis-succinimidylmethylether; TSEA=tris(succinimidylethyl)amine; (BAT-BS)=N-{2-(N', N'bis(2-succinimidoethyl) aminoethyl)}-$N^{6,}N^{9}$,-bis(2-methyl-2-mercaptopropyl)-6,9-diazanonanamide; peptides are linked to BSME, TSEA, (BAT-BS) or (CH$_2$CO)-containing linkers via the free thiol moiety of the unprotected cysteine residue (C) in each peptide. ( . . . )$_2$K represents a covalent bond between the moiety in parenthesis and each of the amino groups (i.e., the α-amino and the sidechain amine) of lysine. (Nε-K) represents covalent linkage at the ε amine rather than at the usual α amino group of the lysine residue.

TABLE II

| Peptides | IC$_{50}$(μM)** | Clot/Blood* |
|---|---|---|
| P357 | 0.079 | 6.3 ± 3.4[5] |
| P667 | 0.081 | 5.9, 5.0[2] |
| P682 | 0.130 | 4.0[1] |
| P317 | 0.036 | 3.8 ± 2.2[3] |
| P381 | 0.035 | 2.5 |
| P154 | 0.30 | 2.0 ± 0.5[3] |
| P246 | 0.85 | 4.4 ± 1.8 |
| P143 | 1.3 | 1.4 |
| P97 | 8 | 1.0 |
| P98 | 15 | 1.7 |
| P63 | 19 | 1.7 |
| P47 | 23 | 1.0 |
| P81 | 25 | 1.8 ± 0.6[3] |
| P32 | 26 | 1.2 ± 0.2[4] |

[1]n = 1;
[2]n = 2;
[2]n = 3;
[4]n = 4;
[5]n = 9
*ratio of (% injected dose/g in a femoral vein thrombus)/(% injected dose/g in blood) at approximately 4 h post-injection of each Tc-99 m labeled reagent in a canine model of DVT
**concentration of reagent that inhibits by 50% the aggregation of human platelets in platelet-rich plasma induced to aggregate by the addition of adenosine diphosphate (ADP)

These results demonstrate that the compounds having an IC$_{50}$ less than or equal to about 1 μM show greater efficacy as scintigraphic imaging agents that compounds having an IC$_{50}$ greater than about 1 μM.

EXAMPLE 4

Scintigraphic Imaging of Deep-Vein Thrombi in Humans in vivo

A series of experiments comprising a pilot human clinical study of one embodiment of the scintigraphic imaging agents of the invention, designated P280, having the chemical structure:

(CH$_2$CO.Y$_D$ApcGDCGGC$_{Acm}$GC$_{Acm}$GGC.amide)$_2$-BSME were performed. These experiments were performed on 9 human patients (6 males, 3 females), ages 30 to 60 years and weighing 63 to 100 kg. Each of the patients presented clinically with the symptoms of deep-vein thrombosis, and the diagnosis was confirmed by physical work-up, ultrasonography and/or contrast venography.

Each patient in the study was administered 10–22 mCi Tc-99m labeled P280 comprising approximately 0.25 mg peptide, by intravenous injection. Scintigraphic imaging was then performed over four hours using a large field-of-view gamma camera equipped with a high-resolution collimator (photopeaked at 140 keV, with a 20%±window). Gamma camera imaging was commenced simultaneously with injection. Anterior images followed by posterior images over the legs were acquired over the first hour, then at 2 and 4 hours post-injection.

Figure 2:
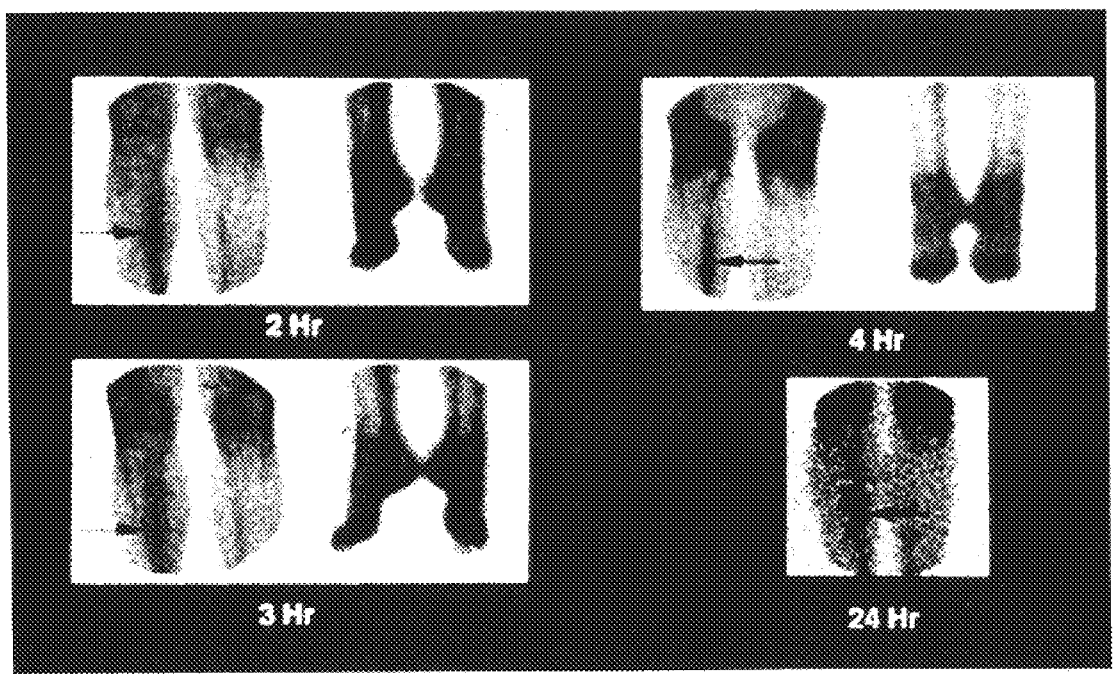
FIG. 2 illustrates scintigraphic imaging of deep-vein thrombi in the calf in human patients using a Tc-99m radiolabel peptide reagent of the invention.

The results of these studies are shown in FIG. 1, which shows thrombus localization in vessels of the lower thigh and FIG. 2, which shows thrombus localization in vessels of the calf. Thrombi so localized are highlighted with an arrow in each Figure. In addition to rapidly and efficiently localizing sites of deep-vein thrombi, this scintigraphic imaging agent was found to clear rapidly from the bloodstream, resulting in less than about 10% of the injected dose remaining in the circulation 1 hour post-injection. Consistent with animal studies, at least 60–70% of the injected dose was found to be cleared by the kidneys. Thrombus visualization was evident as early as 15–30 min after injection, and remained visible for 4–24 hours post-injection. Thrombus visualization correlated well with the clinical diagnosis of deep-vein thrombosis made based on the aforementioned conventional clinical criteria, thrombi being visualized in 8 of the 9 patients studied. The one patient in which a thrombus was not visualized presented with a clinically old thrombus (42 days), which was likely quiescent and hence no longer experiencing platelet turnover at its surface. Finally, no toxicity or other adverse effects of Tc-99m labeled P280 administration were observed in any of these patients.

These results demonstrate that the scintigraphic imaging agents of the invention represents a safe and effective diagnostic reagent for preparing clinically-effective scintigraphic imaging agents useful for clinical, in vivo use for visualizing deep-vein thrombi in humans.

It should be understood that the foregoing disclosure emphasizes certain specific embodiments of the invention and that all modifications or alternatives equivalent thereto are within the spirit and scope of the invention as set forth in the appended claims.

What is claimed is:

1. A thrombus imaging agent comprising:
   a) a reagent comprising
      i) a radiolabel complexing moiety; and
      ii) a platelet glycoprotein IIb/IIIa-binding compound covalently linked to the moiety and having a molecular weight less than 10,000 daltons;
   wherein said reagent is capable of inhibiting human platelet aggregation in platelet-rich plasma by 50% when present at a concentration not greater than about 1 $\mu$M and
   b) a radiolabel.

2. The agent of claim 1, wherein the complexing moiety comprises a single-thiol-containing moiety having a formula:

$$A—CZ(B)—\{C(R^1R^2)\}_n—X$$

wherein
A is H, HOOC, $H_2$NOC, (amino acid or peptide)-NHOC, (amino acid or peptide)-OOC or $R^4$;
B is H, SH, —$NHR^3$, —$N(R^3)$-(amino acid or peptide), or $R^4$;
X is H, SH, —$NHR^3$, —$N(R^3)$-(amino acid or peptide) or $R^4$;
Z is H or $R^4$;
$R^1$, $R^2$, $R^3$ and $R^4$ are independently H or lower straight or branched chain or cyclic alkyl;
n is 0, 1 or 2;
(peptide) is a peptide having between 2 and about 10 amino acids; and
where B is —$NHR^3$ or —$N(R^3)$-(amino acid or peptide), X is SH, and n is 1 or 2;
where X is —$NHR^3$ or —$N(R^3)$-(amino acid or peptide), B is SH, and n is 1 or 2;
where B is H or $R^4$, A is HOOC, $H_2$NOC, (amino acid or peptide)-NHOC, (amino acid or peptide)-OOC, X is SH, and n is 0 or 1;

where A is H or $R^4$, then where B is SH, X is —$NHR_3$ or —$N(R^3)$-(amino acid or peptide) and where X is SH, B is —$NHR^3$ or —$N(R^3)$-(amino acid or peptide);
where X is H or $R^4$, A is HOOC, $H_2$NOC, (amino acid or peptide)-NHOC, (amino acid or peptide)-OOC and B is SH;
where Z is methyl, X is methyl, A is HOOC, $H_2$NOC, (amino acid or peptide)-NHOC, (amino acid or peptide)-OOC, B is SH and n is 0; and
wherein the thiol moiety is in the reduced form and (amino acid) is any primary $\alpha$- or $\beta$-amino acid not containing a thiol group.

3. The agent of claim 2, wherein the complexing moiety is selected from the group consisting of:
   -(amino acid)$^1$-(amino acid)$^2$-{A—CZ(B)—{C($R^1R^2$)}$_n$—X};
   -{A—CZ(B)—{C($R^1R^2$)}$_n$—X}-(amino acid)$^1$-(amino acid)$^2$;
   -(a primary $\alpha,\omega$- or $\beta,\omega$-diamino acid)-(amino acid)$^1$-{A—CZ(B)—{C($R^1R^2$)}$_n$—X}; and
   -{A—CZ(B)—{C($R^1R^2$)}$_n$—X}-(amino acid)$^1$-(a primary $\alpha,\omega$- or $\beta,\omega$-diamino acid),
wherein (amino acid)$^1$ and (amino acid)$^2$ are each independently any naturally-occurring, modified, substituted or altered $\alpha$- or $\beta$-amino acid not containing a thiol group.

4. The agent of claim 1, wherein the reagent is

$CH_2CO$—$Y_D$ApcGDCGGC$_{Acm}$GC$_{Acm}$GGC.amide.

5. The agent of claim 1, wherein the radiolabel is selected from the group consisting of technetium-99m, indium-111, and gallium-68.

6. A complex formed by reacting technetium-99m and a reducing agent with a reagent comprising:
   a) a radiolabel complexing moiety; and
   b) a platelet glycoprotein IIb/IIIa-binding compound covalently linked to the moiety and having a molecular weight less than 10,000 daltons;

wherein said reagent is capable of inhibiting human platelet aggregation in platelet-rich plasma by 50% when present at a concentration not greater than about 1 $\mu$M.

7. The complex of claim 6, wherein the reducing agent is selected from the group consisting of a dithionite ion, a stannous ion, and a ferrous ion.

8. A complex formed by labeling a reagent comprising:
   a) a radiolabel complexing moiety; and
   b) a platelet glycoprotein IIb/IIIa-binding compound covalently linked to the moiety and having a molecular weight less than 10,000 daltons;
wherein said reagent is capable of inhibiting human platelet aggregation in platelet-rich plasma by 50% when present at a concentration not greater than about 1 $\mu$M;
   with technetium-99m by ligand exchange of a prereduced technetium-99m complex.

9. A kit comprising a sealed vial containing:
   a) a predetermined quantity of a reagent comprising:
      i) a radiolabel complexing moiety; and
      ii) a platelet glycoprotein IIb/IIIa-binding compound covalently linked to the moiety and having a molecular weight less than 10,000 daltons;
   wherein said reagent is capable of inhibiting human platelet aggregation in platelet-rich plasma by 50% when present at a concentration not greater than about 1 $\mu$M; and
   b) a sufficient amount of a reducing agent to label the reagent with technetium-99m.

10. A method of making the imaging agent of claim 1, comprising the step of reacting the reagent with Tc-99m in the presence of a reducing agent.

11. The method of claim 10, wherein the reducing agent is selected from the group consisting of a dithionite ion, a stannous ion, and a ferrous ion.

* * * * *